United States Patent [19]

Sircar

[11] 4,397,855

[45] Aug. 9, 1983

[54] 4-(SUBSTITUTED)-α, α-DIMETHYL-1-PIPERAZINE PENTANOIC ACIDS AND DERIVATIVES AS ANTI-ARTERIOSCLEROTIC AGENTS AND METHOD

[75] Inventor: Ila Sircar, Ann Arbor, Mich.

[73] Assignee: Warner-Lambert Company, Morris Plains, N.J.

[21] Appl. No.: 277,578

[22] Filed: Jun. 26, 1981

[51] Int. Cl.$^3$ ............... A61K 31/495; C07D 295/10; C07D 295/16
[52] U.S. Cl. ................... 424/250; 544/392; 544/396; 544/399; 544/358; 542/440
[58] Field of Search ............. 544/392, 399, 358, 396; 424/250; 542/440

[56] References Cited

U.S. PATENT DOCUMENTS

| | | | |
|---|---|---|---|
| 3,658,821 | 4/1972 | Fauran et al. | 544/399 |
| 3,753,984 | 8/1973 | Fauran et al. | 542/440 |
| 4,007,282 | 2/1977 | Mauz et al. | 424/308 |
| 4,125,612 | 11/1978 | Sherlock | 424/250 |
| 4,153,794 | 5/1979 | Ishiguro | 544/358 |
| 4,239,759 | 12/1980 | Gante et al. | 544/106 |

FOREIGN PATENT DOCUMENTS

| | | | |
|---|---|---|---|
| 766588 | 9/1972 | Belgium | 424/250 |
| 42162 | 12/1981 | European Pat. Off. | 424/250 |
| 1445672 | 12/1968 | Fed. Rep. of Germany | 544/392 |
| 140687 | 2/1968 | France | 544/399 |
| 751351 | 2/1970 | France | 424/250 |

OTHER PUBLICATIONS

Maxwell et al., "Effects of Gemfibrozil . . . ", Artery 4(4): 303–313 (1978).
Zikolova et al., "Synthesis of Pyrazine Derivatives", Chem. Abst. 84: 59388v.
Irikura, 1(3–phenylpropyl)–4–(acyl)piperazine, Chem. Abst. 86: 89893q.
Holmes et al., Drugs Affecting Lipid Metabolism, pp. 45–47, and 85 (1969).

Primary Examiner—Donald G. Daus
Assistant Examiner—G. Hendricks
Attorney, Agent, or Firm—Ronald A. Daignault

[57] ABSTRACT

New 4-(substituted-α, α-dimethyl-1-piperazine pentanoic acids and derivatives which are useful as antiarteriosclerotic agents are disclosed. These compounds elevate the high density lipoprotein fraction of cholesterol, and also lower the low density lipoprotein fraction of cholesterol.

17 Claims, No Drawings

4-(SUBSTITUTED)-α, α-DIMETHYL-1-PIPERAZINE PENTANOIC ACIDS AND DERIVATIVES AS ANTI-ARTERIOSCLEROTIC AGENTS AND METHOD

BACKGROUND OF THE INVENTION

Elevated levels of blood cholesterol and blood lipids are conditions which are believed related to the onset of arteriosclerosis. Thus, compounds capable of reducing the levels of these blood constituents are recognized as potentially useful anti-arteriosclerotic agents.

The compounds of the present invention are useful as anti-arteriosclerotic agents and are capable of elevating the high density lipoprotein fraction of cholesterol (HDL-cholesterol,) which effect is known to lower the risk factor of coronary heart disease (Gordon, T. et al., High Density Lipoprotein as a Protective Factor Against Coronary Heart Disease, May 1977, The American Journal of Medicine, Vol. 62, pp. 707–714). Certain compounds of the invention also are able to reduce the low density lipoprotein fraction of cholesterol (LDL-cholesterol), thus further reducing the risk factor of coronary heart disease.

SUMMARY OF THE INVENTION

The invention sought to be patented in its generic chemical compound aspect is a compound having the structural formula I:

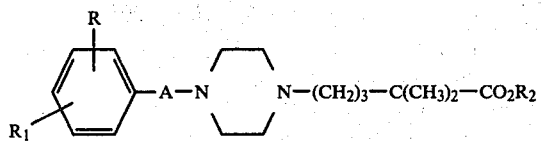

wherein R and $R_1$ may be the same or different and are hydrogen, halogen, nitro, alkyl of from 1 to 6 carbon atoms, alkoxy of from 1 to 6 carbon atoms, triflouromethyl, carboxylic acyl of from 1 to 6 carbon atoms, or 1-hydroxyalkyl of from 1 to 6 carbon atoms; $R_2$ is hydrogen, alkyl of from 1 to 6 carbon atoms, or a pharmaceutically acceptable cation; A is a direct bond, methylene, benzal, $SO_2$, CH=CH—CO, CO, or NHCO, and the pharmaceutically acceptable salts thereof.

The invention sought to be patented in a first subgeneric chemical compound aspect is a compound having the structural formula II,

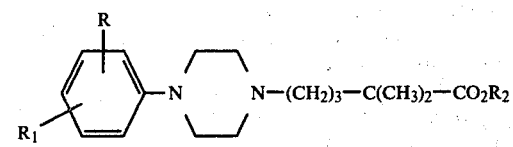

wherein R, $R_1$ and $R_2$ are defined above, and the pharmaceutically acceptable salts thereof.

The invention sought to be patented in a second subgeneric chemical compound aspect is a compound having the structural formula III,

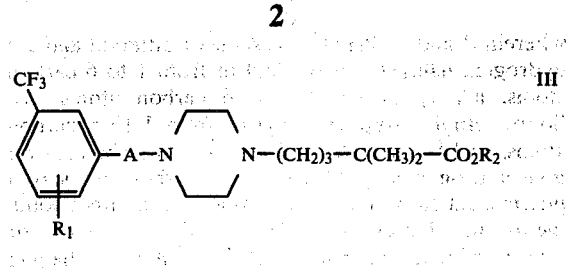

wherein A, $R_1$ and $R_2$ are defined above, and the pharmaceutically acceptable salts thereof.

The invention sought to be patented in a third subgeneric chemical compound aspect is a compound having the structural formula IV

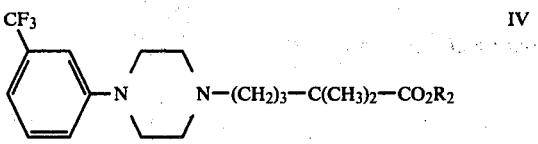

wherein $R_2$ is defined above, and the pharmaceutically acceptable salts thereof.

The invention sought to be patented in a first generic chemical process aspect is a process for preparing a chemical compound having the structural formula I

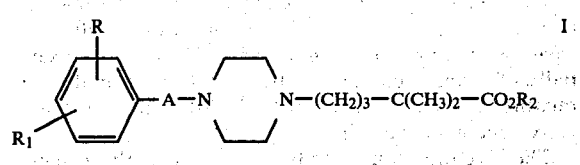

wherein R and $R_1$ may be the same or different and are hydrogen, halogen, nitro, alkyl of from 1 to 6 carbon atoms, triflouromethyl, carboxylic acyl of from 1 to 6 carbon atoms, or 1-hydroxyalkyl of from 1 to 6 carbon atoms; $R_2$ is hydrogen, alkyl of from 1 to 6 carbon atoms, or a pharmaceutically acceptable cation; A is a direct bond, methylene, benzal, $SO_2$, CH=CH—CO, CO, or NHCO; which comprises reacting a substituted piperazine of the structural formula V

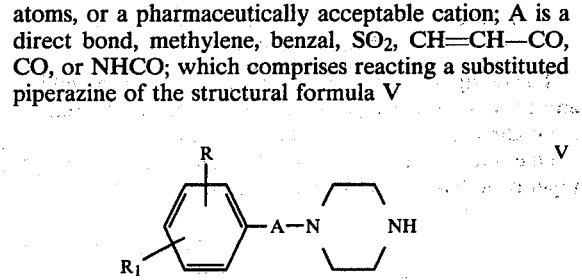

with a 2,2-dimethyl pentanoic acid derivative having the structural formula VI

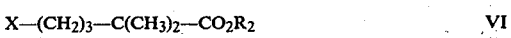

wherein R—$R_2$ and A are defined above, and X is halogen.

The invention sought to be patented in a second generic chemical process aspect is a process for preparing a compound having the structural formula I

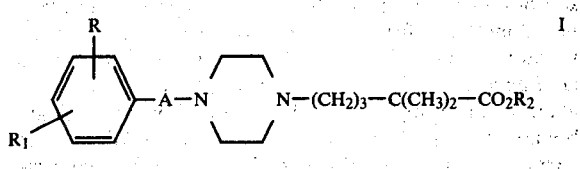

wherein R and $R_1$ may be the same or different and are hydrogen, halogen, nitro, alkyl of from 1 to 6 carbon atoms, alkoxy of from 1 to 6 carbon atoms, triflouromethyl, carboxylic acyl of from 1 to 6 carbon atoms, or 1-hydroxyalkyl of from 1 to 6 carbon atoms; $R_2$ is hydrogen, alkyl of from 1 to 6 carbon atoms, or a pharmaceutically acceptable cation; A is a direct bond, methylene, benzal, $SO_2$, CH=CH—CO, CO, or NHCO; which comprises reacting a piperazine having the structural formula VII

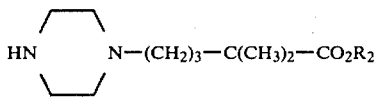   VII with a compound having the structural formula VIII

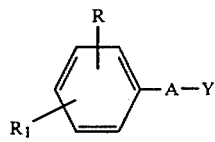   VIII wherein R—$R_2$ and A are defined above and Y is a leaving group.

The invention sought to be patented in a pharmaceutical composition aspect is a composition useful for treating artereosclerosis in a mammal consisting essentially of a compound having the structural formula I or mixtures thereof, in combination with a pharmaceutically acceptable carrier.

The invention sought to be patented in a pharmaceutical method aspect is a method for treating arteriosclerosis in a mammal in need of such treatment; which comprises administering an effective amount of the above defined pharmaceutical composition to said mammal.

DESCRIPTION OF THE PREFERRED EMBODIMENTS

The compounds of the invention may be prepared by any of several processes which are to be considered as equivalent for purposes of this invention.

One such process involves the reaction between a piperazine having the structural formula V,

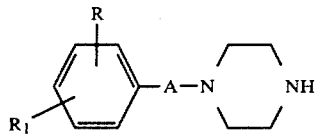   V with a 2,2-dimethylpentanoic acid derivative having the structural formula VI

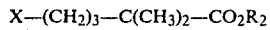   VI wherein R—$R_2$, A and X are defined above.

This reaction is most conveniently carried out in solution in a non-reactive solvent such as a lower alkanol, dimethylsulfoxide or dimethylformamide at a temperature of up to about 120° C. in the presence of an acid acceptor such as a tertiary amine, pyridine or an alkali metal or alkaline earth metal carbonate or bicarbonate. In a preferred process, the above reaction is carried out in dimethylformamide solution at a temperature of about 70°–80° C. in the presence of potassium carbonate. In this preferred procedure, the reaction is substantially complete in about 18 hours.

The monosubstituted piperazines of structural formula V may be prepared as described in J.Med.Chem., 21, 1301 (1978) or by obvious variations thereof. The carboxylic acid esters and acids of structural formula VI may be prepared as described in U.S. Pat. No. 3,674,836 or by obvious variations thereof.

In a second process for preparing the compounds of the invention, an N-substituted piperazine of the structural formula VII

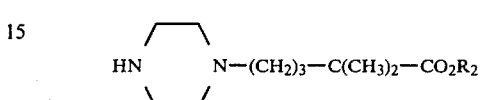   VII is reacted with compound having the structural formula VIII

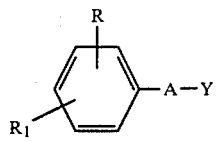   VIII wherein R—$R_2$, A and Y are defined above.

Compound VII may be conveniently prepared from N-benzylpiperazine and a compound of structural formula VI by a substantially indentical procedure described above for the reaction of compounds V and VI. The product of this reaction is debenzylated by procedures well known to those skilled in the art such as hydrogenation over a Pd on carbon catalyst to produce the compound of structural formula VII. The requisite N-benzylpiperazine is commercially available, for example from Aldrich Chemical Company, Milwaukee, Wis. 53233, U.S.A. The reaction between Compounds VII and VIII is carried out in a non-reactive solvent in the presence of an acid acceptor such as a tertiary amine, pyridine or an alkali metal or alkaline earth metal carbonate or bicarbonate. In a preferred procedure Compound VII and VIII are reacted in methylene chloride at room temperature in the presence of triethylamine for about 15 hours. The leaving groups represented by substituent Y are well known to those skilled in the art. Examples of such leaving groups are chlorine, bromine and the like. The preferred leaving group is chlorine.

The compounds of the invention wherein $R_2$ is hydrogen form pharmaceutically acceptable salts with both organic and inorganic acids and bases. Examples of suitable acids for salt formation are hydrochloric, sulfuric, phosphoric, acetic, citric, oxalic, malonic, salicylic, malic, fumaric, succinic, ascorbic, maleic, methansulfonic and the like. The salts are prepared by contacting the free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

Examples of suitable bases for salt formation are sodium hydroxide, sodium carbonate, sodium bicarbonate, potassium hydroxide, calcium hydroxide, ammonia, organic amines and the like. The salts are prepared by contacting the free acid form with an equivalent amount of the desired base in the conventional manner. The free acid forms may be regenerated by treating the salt form with an acid. For example, dilute aqueous acid solutions may be utilized. Dilute aqueous hydrochloric acid, sulfuric acid or acetic acid are suitable for this purpose. The free acid forms differ from their respective salt forms somewhat in certain physical properties such as solubility in polar solvents, but the salts are otherwise equivalent to their respective free acid forms for purposes of the invention.

The compounds of the invention wherein $R_2$ is alkyl of from 1 to 6 carbon atoms form pharmaceutically acceptable salts with both organic and inorganic acids. Examples of suitable acids and methods of preparation of the salts are identical to those given above.

The compounds of the invention can exist in unsolvated as well as solvated forms, including hydrated forms. In general, the solvated forms, with pharmaceutically acceptable solvents such as water, ethanol and the like are equivalent to the unsolvated forms for purposes of the invention.

The term halogen is intended to include fluorine, chlorine, bromine and iodine.

The alkyl and alkoxy groups contemplated by the invention, unless specified, otherwise comprise both straight and branched carbon chains of from 1 to about 6 carbon atoms. Representative of such groups are methyl, ethyl, isopropyl, butyl, pentyl, 3-methylpentyl, methoxy, ethoxy, i-propoxy, t-butoxy, n-hexoxy, 3-methylpentoxy and the like.

The compounds of the invention are new chemical substances of value as pharmacological agents for the treatment of arterosclerosis in warm-blooded animals. The anti-artereosclerotic activity of representative compounds of the invention was established by the Screening procedure described in Maxwell, R. E., Nawrocki, J. W., and Uhlendorf, P. D., Artery, 1, 303 (1978). This procedure is incorporated by reference herein. Utilizing this procedure, the following results were obtained for representative compounds of this invention.

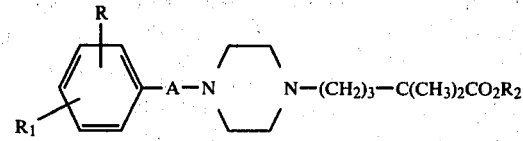

| R | $R_1$ | $R_2$ | A | Cholesterol | Triglyceride | HDL | LDL | Increase Liver wt. |
|---|---|---|---|---|---|---|---|---|
| H | 3-$CF_3$ | $CH_3$ | Bond | −42 | −16 | +222 | −54 | 0 |
| H | 4-$CF_3$ | $CH_3$ | Bond | −36 | −35 | +349 | −66 | +31 |
| H | 4-Cl | $CH_3$ | Bond | −68 | −40 | +159 | −85 | +25 |
| H | 4-$OCH_3$ | $CH_3$ | Bond | −47 | 0 | +54 | −53 | +6 |
| H | 3-$CH_3$ | $CH_3$ | Bond | −43 | 0 | +52 | −49 | +7 |
| H | 4-$COCH_3$ | $CH_3$ | Bond | −32 | −22 | +101 | −40 | 0 |
| H | 4-CH(OH)—$CH_3$ | $CH_3$ | Bond | −34 | −18 | +132 | −43 | +9 |
| 3-Cl | 4-Cl | $CH_3$ | Bond | −65 | −33 | +127 | −89 | +7 |
| 3-$CF_3$ | 4-Cl | $CH_3$ | Bond | −49 | −49 | +155 | −75 | +9 |
| H | H | $CH_3$ | $CH_2$ | 0 | 0 | +61 | 0 | 0 |
| H | 4-Cl | $CH_3$ | CH—Ph | −42 | 0 | +65 | −46 | 0 |
| H | 4-$CH_3$ | $CH_3$ | $SO_2$ | 0 | +16 | +67 | 0 | +8 |
| H | H | $CH_3$ | CH=CHCO | −47 | 0 | +213 | −64 | +19 |

An increase in liver weight is indicative of hepatomegaly and hepatic peroxisome proliferation. Both are undesirable side effects of the known anti-artereosclerotic agents, Reddy, J. F., and Krishnakantha, T. P., Science, 190, 787 (1975).

The compounds of the invention can be prepared and administered in a wide variety of oral and parenteral dosage forms. It will be clear to those skilled in the art that the following dosage forms may comprise as the active component, either a compound of formula I, or a corresponding pharmaceutically acceptable salt of a compound of formula I, or a mixture of such compounds and/or salts.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methyl cellulose, sodium carboxymethyl cellulose and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these packaged form.

The quantity of active compound in a unit dose of preparation may be varied or adjusted from 1 mg to 100 mg according to the particular application and the potency of the active ingredient.

In therapeutic use as agents for treating artereosclerosis, the compounds utilized in the pharmaceutical method of this invention are administered at the initial dosage of about 10 mg to about 250 mg per kilogram daily. A daily dose range of about 10 mg to about 30 mg per kilogram is preferred. The dosages, however, may be varied depending upon the requirements of the patient, the severity of the condition being treated and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following non-limiting examples illustrate the inventor's preferred methods for preparing the compounds of the invention.

EXAMPLE 1

A mixture of N-($\alpha,\alpha,\alpha$-trifluoro-m-tolyl)piperazine (8.0 g), anhydrous potassium carbonate (6.0 g), and methyl-5-bromo-2,2-dimethyl pentanoate (8.8 g) in N,N-dimethylformamide (100 ml) is heated at 70°-80° for 17-18 hours. The solution is cooled, filtered from the inorganic salts, and N,N dimethylformamide is distilled under reduced pressure. The residue is distilled under high vacuum to yield 14.0 g of the product, methyl 4-[3(trifluoromethyl)phenyl]-$\alpha,\alpha$-dimethyl-1-piperazine pentanoate, bp 152°-154°/0.1 mm pressure of mercury.

EXAMPLE 2

Following the procedure of example 1, with the substitution of N-($\alpha,\alpha,\alpha$-trifluoro-p-tolyl)piperazine in place of N-($\alpha,\alpha,\alpha$-trifluoro-m-tolyl)piperazine, the product obtained is methyl 4-[4-trifluoromethyl)phenyl]-$\alpha,\alpha$-dimethyl-1-piperazine pentanoate, mp 44°-45° C. following crystallization from hexane.

EXAMPLE 3

Following the procedure of example 1, with the substitution of N-(3,4-dichlorophenyl)piperazine hydrochloride in place of N-($\alpha,\alpha,\alpha$-trifluoro-m-tolyl)piperazine, the product obtained is methyl 4-(3,4-dichlorophenyl)-$\alpha,\alpha$-dimethyl-1-piperazine pentanoate, bp 190°/0.1 mm pressure of mercury.

EXAMPLE 4

Following the procedure of example 1, with the substitution of N-[4-chloro-3($\alpha,\alpha,\alpha$-trifluoromethyl)phenyl]piperazine hydrochloride in place of N-($\alpha,\alpha,\alpha$-trifluoro-m-tolyl)piperazine, the product obtained is methyl 4[4-chloro-3-(trifluoromethyl)phenyl]-$\alpha,\alpha$-dimethyl-1-piperazine pentanoate, bp 170°-2°/0.1 mm pressure of mercury.

EXAMPLE 5

Following the procedure of example 1, with the substitution of N-(4-chlorophenyl)piperazine dihydrochloride in place of N-($\alpha,\alpha,\alpha$-trifluoro-m-tolyl)piperazine, the product obtained is methyl 4-(4-chlorophenyl)-$\alpha,\alpha$-dimethyl-1-piperazine pentanoate, mp 47°-48° C. following crystallization from hexane.

EXAMPLE 6

Following the procedure of example 1, with the substitution of N-(4-acetylphenyl)piperazine in place of N-($\alpha,\alpha,\alpha$-trifluoro-m-tolyl)piperazine, the product obtained is methyl 4-(4-acetylphenyl)-$\alpha,\alpha$-dimethyl-1-piperazine pentanoate, mp 54°-56° C. following crystallization from isopropyl ether.

EXAMPLE 7

3.0 g of methyl 4-(4-acetylphenyl)$\alpha,\alpha$-dimethyl-1-piperazine pentanoate is reduced with sodiumborohydride (0.4 g) in methanol at room temperature. The usual work up yield 2.5 g of the product methyl 4-[4-(1-hydroxyethyl)phenyl]-$\alpha,\alpha$-dimethyl-1-piperazine pentanoate, mp 82°-83° C.

EXAMPLE 8

Following the procedure of example 1, with the substitution of N-phenyl piperazine in place of N-($\alpha,\alpha,\alpha$-trifluoromethyl-m-tolyl)piperazine, the product obtained is methyl $\alpha,\alpha$-dimethyl-4-phenyl-1-piperazine pentanoate, bp 180°/0.5 mm pressure of mercury.

EXAMPLE 9

Following the procedure of example 1, with the substitution of N-benzylpiperazine in place of N-($\alpha,\alpha,\alpha$-trifluoromethyl-m-tolyl)piperazine, the product obtained is methyl $\alpha,\alpha$-dimethyl-4-(phenylmethyl)-1-piperazine pentanoate, bp 150°/0.5 mm pressure of mercury.

EXAMPLE 10

Following the procedure of example 1, with the substitution of N-(p-chlorobenzhydryl)piperazine in place of N-($\alpha,\alpha,\alpha$-trifluoromethyl-m-tolyl)piperazine, the product obtained is 4-[(4-chlorophenyl)phenyl methyl]-$\alpha,\alpha$-dimethyl-1-piperazine pentanoic acid, mp 183°-184° C. following crystallization from tetrahydrofuran-isopropyl ether.

EXAMPLE 11

A solution of cinnamoyl chloride (3.32 g) in methylene chloride (25 ml) is added dropwise to a solution of methyl, α,α-dimethyl-1-piperazinepentanoate (4.56 g) in methylene chloride (25 ml) containing triethylamine (2.0 g) and the mixture is stirred overnight at room temperature. The solution is washed with water, dried, and distilled to yield the product methyl α,α-dimethyl-4-(1-oxo-3-phenyl-2-propenyl)-1-piperazine pentanoate, mp 76° following crystallization from isopropyl ether.

EXAMPLE 12

Following the procedure of example 11, with the substitution of p-toluene sulfonylchloride in place of cinnamoyl chloride, the product obtained is methyl α,α-dimethyl-4-[(4-methylphenyl)sulfonyl]-1-piperazine pentanoate.

I claim:

1. A compound having the structural formula

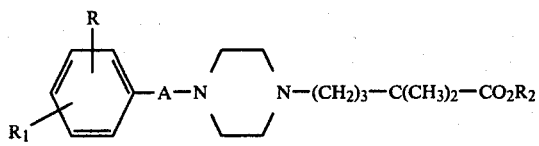

wherein R and $R_1$ may be the same or different and are hydrogen, halogen, alkyl of from 1 to 6 carbon atoms, trifluoro methyl, carboxylic acid of from 1 to 3 carbon atoms, or 1-hydroxyalkyl of from 1 to 3 carbon atoms; $R_2$ is hydrogen, alkyl of from 1 to 3 carbon atoms, or a pharmaceutically acceptable cation; A is a direct bond, methylene, benzal, CH=CH—CO, and the pharmaceutically acceptable salts thereof.

2. The compounds defined in claim 1 which have the structural formula

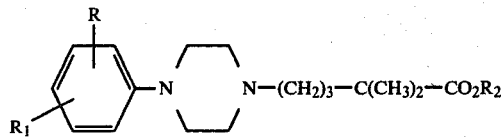

and the pharmaceutically acceptable salts thereof.

3. The compounds defined in claim 1 which have the structural formula

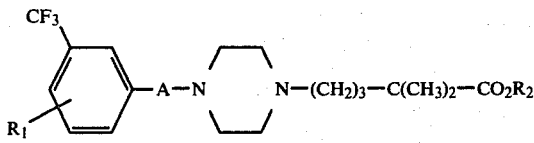

and the pharmaceutically acceptable salts thereof.

4. The compounds defined in claim 1 which have the structural formula

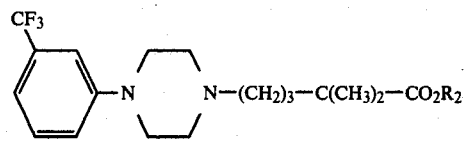

and the pharmaceutically acceptable salts thereof.

5. The compound defined in claim 1 which is 4-[3-(trifluoromethyl)phenyl]-α,α-dimethyl-1-piperazine pentanoate, and the pharmaceutically acceptable salts thereof.

6. The compound defined in claim 1 which is methyl 4-[4-trifluoromethyl)phenyl]-α,α-dimethyl-1-piperazine pentanoate, and the pharmaceutically acceptable salts thereof.

7. The compound defined in claim 1 which is methyl 4-(3-dichlorophenyl)-α,α-dimethyl-1-piperazine pentanoate, and the pharmaceutically acceptable salts thereof.

8. The compound defined in claim 1 which is methyl 4-[4-chloro-3-(trifluoromethyl)phenyl]-α,α-dimethyl-1-piperazine pentanoate, and the pharmaceutically acceptable salts thereof.

9. The compound defined in claim 1 which is methyl 4-(4-chlorophenyl)-α,α-dimethyl-1-piperazine pentanoate, and the pharmaceutically acceptable salts thereof.

10. The compound defined in claim 1 which is methyl 4-(4-acetylphenyl)-α,α-dimethyl-1-piperazine pentanoate, and the pharmaceutically acceptable salts thereof.

11. The compound defined in claim 1 which is methyl 4-[4-(1-hydroxyethyl)phenyl]-α,α-dimethyl-1-piperazine pentanoate, and the pharmaceutically acceptable salts thereof.

12. The compound defined in claim 1 which is methyl α,α-dimethyl-4-phenyl-1-piperazine pentanoate, and the pharmaceutically acceptable salts thereof.

13. The compound defined in claim 1 which is methyl α,α-dimethyl-4-(phenylmethyl)-1-piperazine pentanoate, and the pharmaceutically acceptable salts thereof.

14. The compound defined in claim 1 which is 4-[(4-chlorophenyl)phenyl methyl]-α,α-dimethyl-1-piperazine pentanoic acid, and the pharmaceutically acceptable salts thereof.

15. The compound defined in claim 1 which is methyl α,α-dimethyl-4-(1-oxo-3-phenyl-2-propenyl)-1-piperazine pentanoate, and the pharmaceutically acceptable salts thereof.

16. A composition useful for treating artereosclerosis in a mammal consisting essentially of a compound defined in claim 1 or mixtures thereof, in combination with a pharmaceutically acceptable carrier.

17. A method for treating arteriosclerosis in a mammal in need of such treatment; which comprises administering an effective amount of the pharmaceutical composition defined in claim 16 to said mammal.

* * * * *